United States Patent
Salley

Patent Number: 6,142,961
Date of Patent: Nov. 7, 2000

[54] VENOUS GRADIENT SUPPORT DEVICE

[76] Inventor: Frank Salley, 1002 Chastain Park Ct., Atlanta, Ga. 30342

[21] Appl. No.: 09/144,029

[22] Filed: Aug. 27, 1998

[51] Int. Cl.[7] .............................. A61H 1/00; A61F 13/00
[52] U.S. Cl. .................................. 601/1; 601/11; 602/65
[58] Field of Search ............................... 602/62, 63, 64, 602/65, 66, 75–77; 2/16, 22; 601/11, 5, 1

[56] References Cited

U.S. PATENT DOCUMENTS

| | | | |
|---|---|---|---|
| 2,113,253 | 4/1938 | Gray | 601/609 |
| 2,267,070 | 12/1941 | Baldwin | 602/62 |
| 4,497,070 | 2/1985 | Cho | 2/22 |
| 4,541,418 | 9/1985 | Kirby | 601/1 |
| 5,263,923 | 11/1993 | Fujimoto | 602/62 |

OTHER PUBLICATIONS

U.S. Patent Application Serial No. 042,007 to Frank Salley, titled "Venous Gradient Support Device".

*Primary Examiner*—Gary Jackson

[57] ABSTRACT

A venous pressure gradient support device to be worn over a surface portion of the human body to prevent or remedy varicose veins. The device includes a container configured for receiving and retaining a plurality of beads. Preferably, the beads are glass spherical beads and the container is an envelope having a flap which may be folded over to retain the beads in the envelope. The envelope of beads may be worn underneath a support garment such as support hose so that the envelope filled with beads is pressed to the surface portion of the human body. The envelope of beads conforms to the irregular shape of the human body and the beads take on a pressure gradient to balance the blood pressure at the surface portion of the human body.

11 Claims, 1 Drawing Sheet

VENOUS GRADIENT SUPPORT DEVICE

TECHNICAL FIELD

This invention relates generally to venous return and particularly to a wearing article for treating chronic venous insufficiency of lower human extremities.

BACKGROUND OF THE INVENTION

Veins are blood vessels which return blood to the heart in the circulatory system. Veins are flexible tubes which are divided into compartments by one-way valves. Blood is pumped back to the heart when a skeletal muscle contracts and compresses a compartment, forcing its blood to flow through the valve close to the heart toward the heart and forcing the other valve, the one farther from the heart, to close, allowing no blood to flow away from the heart. A varicose vein is a vein in which at least one valve is destroyed, allowing blood to flow away from the heart.

The pressure on a valve farther from the heart but next to a destroyed valve is greater than the pressure on a valve next to a good valve. The next farther valve fails more quickly. Thus a series of valves can fail, each valve failing more quickly than its predecessor, because the pressure increases on each succeeding valve farther from the heart with the failure of each preceding, closer valve. This pressure that increases as the distance from the heart increases is called a pressure or gravity gradient.

The gradient can be compensated for by a person's standing in a pool of liquid with its specific gravity greater than or equal to that of blood. The gravity gradient of blood within a varicose vein is thus closely matched by the gravity gradient of the liquid. Pressure of the blood is nearly duplicated by the pressure of the liquid. However, a person can tolerate exposure to water for only a few hours.

Venous gradient support garments, often called support hose, are elastic garments wound to duplicate a person's standing in such a liquid. They are tight at the foot and loose at the top. They are used late to try to relieve symptoms of varicose veins and early to try to prevent their occurrence. Two such garments are manufactured by Jobst and Camp.

A sea snake, for example, has its blood pressure balanced by the pressure of its surrounding saltwater, not a strong venous system. Removed from its watery surround and suspended by its head, the sea snake will faint since its blood will flow from its head. Held by its head, a sea snake could have been Aaron's staff.

The pressure-gradient support-garments fail to duplicate the pressure of submersion in water. The garments do not conform to the irregular shapes of the human anatomy the way water will. For example, the material of the garments bridges between the protuberances of the ankle bone and the heel and does not provide pressure to the region below it the way standing in water will. It in fact causes the very problems the use of the support garments is supposed to eliminate: pooling of blood, bleeding from the capillaries and perhaps formation of chronic and often enlarging ulcers.

One invention, such as that taught by U.S. Pat. No. 2,113,253 to Gray, is large, unmanageable (requires the assistance of another to use) restrictive, expensive and of no greater value than bed rest with elevation of the feet above the heart. It severely limits a person's ability to perform normal daily activities.

The present invention is small, manageable, inexpensive and unrestrictive. It allows normal functioning and exercising.

SUMMARY OF THE INVENTION

The present invention solves the above-identified problems by providing a venous pressure gradient support device in the form of a wearing article that conforms to the human anatomy and prevents the occurrence of varicose veins as well as relieves their symptoms. The present invention seeks to provide a wearing article that is worn on a selected surface portion of the human body and takes on a proper gradient to balance the blood pressure at the selected surface portion of the human body.

Generally described, the venous gradient support device of the present invention comprises a container configured for receiving and retaining a plurality of beads. Preferably, the container is an envelope having a flap and the beads are spherical glass beads. Because the beads in the envelope are free to move, the beads are able to conform to the irregular shape of the human anatomy when worn against the selected surface portion of the human body. Therefore, the beads are able to apply pressure and assume a gradient to balance the blood pressure at the selected surface portion.

In accordance with one aspect of the invention, the device is worn underneath a support garment and against the selected surface portion of the human body. Because support garments themselves can not apply pressure to concave regions created between the support garment and the selected surface portion of the human body, the venous gradient support device is worn underneath the support garment in the concave regions so that pressure may be applied to the selected surface portion.

DETAILED DESCRIPTION

Figure 1:
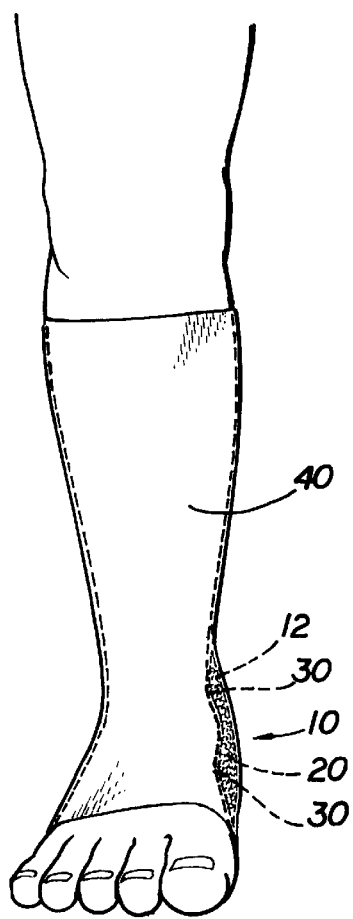
FIG. 1 is a front view of a lower leg wearing support hose and with a venous pressure gradient device over the ankle.

While refering to FIG. 1, the invention comprises a venous pressure gradient support device 10 having a container 12, made of a material strong enough to support the pressure gradient without rupture and permeable enough to pass perspiration (such a material is brand-name "Tyvek"). The container 12 is partially filled with a collection of vanishingly small spherical glass beads (BLAST MEDIA) 20, which volume for volume weigh close to blood, and shape themselves to fit a region of application 30, on the side of and adjacent an ankle, commonly referred to as a concave region or a concavity. The support device 10 may be worn beneath a venous gradient support garment 40.

Figure 2:
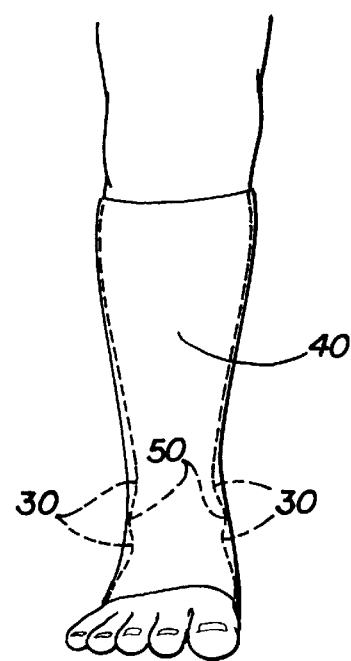
FIG. 2 is a front view of a lower leg wearing support hose without the venous pressure gradient device wherein the support hose does not by itself conform to the irregular shape of the ankle.

Imagine the support garment 40 alone in FIG. 2. Notice that it cannot come into contact with all parts of the leg, namely the concave regions 30 adjacent the ankle 50. The support hose cannot apply pressure to those concave regions 30 of three dimensions because the material of the hose bridges over the volume.

Imagine the support garment 40 with the container 12 of sperical glass beads 20 applied in the concavity 30 in FIG.

Figure 4:
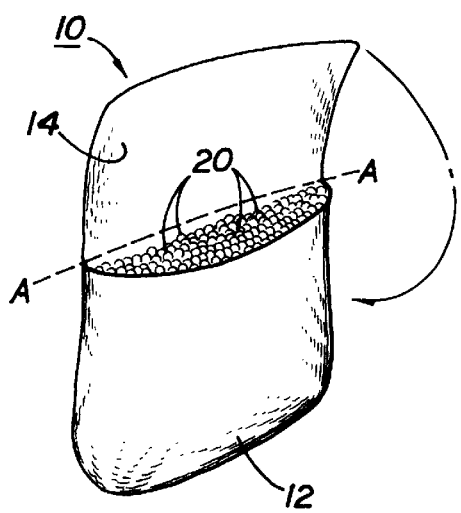
FIG. 4 is a perspective view of an envelope-type container of the venous pressure gradient support device wherein the envelope is filled with beads.
Figure 3:
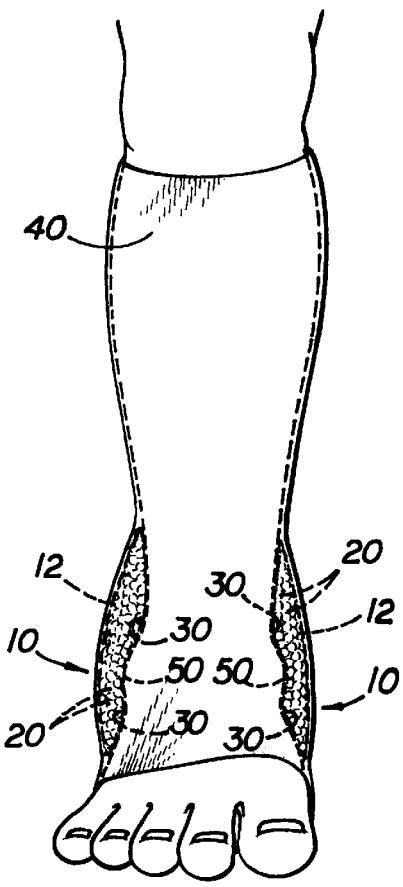
FIG. 3 is a front view of a lower leg wearing support hose and having a pair of venous pressure gradient support devices between the support hose and the sides of the ankle.

3. In this embodiment, the container 12 is an envelope having a flap 14. The flap 14 on the envelop may be folded along line AA as shown in FIG. 4. The sperical glass beads 20 take on the proper gradient to balance the pressure of the blood, just as standing in water. Since the glass beads 20 have nearly a zero angle of repose (the steepest angle a collection of particles can be made to take with horizontal with out support; the angle of repose for table salt is about 45 degrees and the angle of repose for water is of course zero), they behave as a liquid and will change shape as required during articulated movement. The collection of sperical glass beads does not start and stop abruptly; it fills the region as an easement, tapering smoothly from the beginning to the end of the concavity 30. The container 12 is made of a material that is strong and is permeable. It allows passage of perspiration into the garment, preventing the accumulation of pools under it, and is sufficiently strong to not rupture under the high pressure required to balance the pressure gradient. One such material is that of the brand-name "Tyvek."

It is thus seen that a new venous pressure-gradient support device 10 is provided which overcomes restrictions and limitations associated with those of the prior art. It should be understood that the just described embodiments merely illustrate principles of the invention in preferred form. Many modifications, additions, and deletions may be made thereto without departure from the spirit and scope of the invention as set forth in the following claims.

What are claimed are:

1. An envelope made of a strong, permeable material sized to fit over a concave side of a human ankle, and beneath a venous support stocking; and filled with spherical glass beads.

2. A garment for supporting an articulated region of an animal body including a venous gradient support hose incorporating an envelope made of a strong, permeable material sized to fit over a concave side of a human ankle, and beneath a venous support stocking, and filled with spherical glass beads.

3. A wearing article for providing venous gradient support to a surface portion of a human body, comprising:
   a plurality of beads;
   a container for receiving and retaining said beads, said container configured for wearing in pressed relation to the surface portion of the human body such that said container filled with said beads conforms to the surface portion of the human body and said beads take on a proper gradient to balance the blood pressure at the surface portion of the human body.

4. The wearing article of claim 3, wherein said beads are spherical.

5. The wearing article of claim 3, wherein said container is an envelop having a flap.

6. The wearing article of claim 3, wherein said container is made of a permeable material.

7. The wearing article of claim 3, wherein the volume of said beads changes shape during movement.

8. The wearing article of claim 3, wherein said container filled with said beads is configured to be worn underneath a venous support garment.

9. An article for providing venous gradient support to a surface portion of a human body, comprising:
   a plurality of beads; and
   means for maintaining said beads in pressed relation to the surface portion of the human body such that said beads conform to the surface portion of the human body and take on a proper gradient to balance the blood pressure at the surface portion of the human body.

10. The article of claim 9, wherein said means for maintaining said beads in pressed relation to the surface portion comprises a support garment.

11. The article of claim 9, wherein said means for maintaining said beads in pressed relation to the surface portion comprises a container for receiving and retaining said beads and a support garment, said container filled with said beads maintained between said support garment and the surface portion of the human.

* * * * *